United States Patent [19]
De Gruijter

[11] Patent Number: 5,244,519
[45] Date of Patent: Sep. 14, 1993

[54] COATING MATERIAL FOR AND METHOD OF INHIBITING PATHOGENIC AND SAPROPHITIC ORGANISMS

[75] Inventor: Wilhelmus A. E. M. De Gruijter, Zwijndrecht, Belgium

[73] Assignee: Angli Holding B.V., Rotterdam, Netherlands

[21] Appl. No.: 899,485

[22] Filed: Jun. 16, 1992

Related U.S. Application Data

[63] Continuation of Ser. No. 493,464, Mar. 14, 1990, abandoned, which is a continuation-in-part of Ser. No. 259,755, Oct. 19, 1988, abandoned.

[30] Foreign Application Priority Data

Nov. 12, 1987 [BE] Belgium .............................. 08701272

[51] Int. Cl.⁵ .............................................. B32B 31/00
[52] U.S. Cl. ..................................... 156/71; 156/332; 156/334; 428/344; 428/907
[58] Field of Search ................. 428/40, 337, 339, 344, 428/356, 907

[56] References Cited

U.S. PATENT DOCUMENTS

| | | | |
|---|---|---|---|
| 2,808,352 | 10/1957 | Coleman | 428/356 |
| 3,507,676 | 4/1970 | McMahon | 428/907 |
| 3,761,334 | 9/1973 | Zondek | 428/337 |
| 4,496,441 | 1/1985 | Bagnulo | 428/40 |
| 4,654,697 | 2/1987 | Torigoe | 428/344 |

*Primary Examiner*—Jenna L. Davis
*Attorney, Agent, or Firm*—Michael J. Striker

[57] ABSTRACT

A coating zinc material for inhibiting pathogenic and saprophitic microorganisms on indoor surfaces of locations of medical and similar facilities.

17 Claims, No Drawings

COATING MATERIAL FOR AND METHOD OF INHIBITING PATHOGENIC AND SAPROPHITIC ORGANISMS

This is a continuation of application Ser. No. 493,464 filed Mar. 14, 1990 now abandoned, which is a continuation in part of Ser. No. 259,755, filed Oct. 19, 1988, now abandoned.

BACKGROUND OF THE INVENTION

The present invention relates to a coating material for and a method of inhibiting pathogenic and saprophitic organisms.

Particularly, the present invention relates to an anti-bacterial, anti-virulent, anti-fungal and anti-mold coating material, or a coating material which inhibits the formation of bacteria, viruses, fungi and mildews on indoor surfaces of medical facilities and the like, or in other words to a coating material which prevents and-/or discourages the rapid accretion and multiplication of pathogenic and saprophitic organisms on indoor surfaces of medical and other similar facilities. More particularly, the present invention relates to a coating material that comprises a zinc foil, and a self-adhesive electro-conductive layer applied to the zinc foil.

It is well known that it is necessary to continuously combat pollutions which are caused by pathogenic and saprophitic organisms, especially in surroundings that have a tendency to the formation and accretion of such pollutions. Operating, anesthesia, reanimation rooms and transplantation departments of hospitals as well as chemical laboratories which handle, store and analyze biological samples especially of a pathological nature are very susceptible to infections and pollutions caused by pathogenic and saprophitic organisms. This is also true for sterilized rooms used in microbiology and vegetable micropropagation laboratories, and generally for structures where agricultural or elementary biotechnologies are used such as climatic cells, growth rooms, industrial laboratories for the treatment of foodstuffs, etc. The danger of infection caused by pathogenic and saprophitic organisms also takes place in a large degree in environments and containers where infected objects are stored, and where such objects come into physical contact with personnel compelled to handle the same. These environments in particular involve hospital laundries, as well as containers for the transportation of laundry.

It is well known that such infections can be prevented and/or reduced in the most effective way by taking preventive measures. One of the well-known measures is treatment of the potentially infected objects by gamma or ultraviolet radiation. This solution, however, has the disadvantage in that it can be practised only to a limited extent due to technical-economic reasons and the safety of the personnel. Another preventive measure which is used the most for small and large rooms is painting of walls and ceilings with an anti-bacterial and mildew-resistant paint. The paints are intended to prevent multiplication of bacteria and pathogenic germs and/or the increase of the possible mildew affection for a relatively long period. Also a water-resistant paint can be applied as a preventive measure.

The above-specified paints possess the disadvantage in that in order to keep their efficiency they must be cleaned frequently, for example by washing the painted walls, etc. It has been noted that in laboratories and especially in the microbiology practice area, numerous slashes of organic material infected with pathogenic germs very easily appear in and around the working area. These spots which are generally rather thick create a kind of organic protective coating which greatly reduces the anti-bacterial effect of the paint, due to the fact that the commonly used paints react against it insufficiently.

According to another preventive measure, walls and other surfaces can be covered with water-resistant tiles which similarly to the aforementioned water-resistant paints are to be washed off daily with a detergent and a disinfectant. Such covering has the disadvantage in that it is too expensive and the joints of the tiles are difficult to clean with a detergent so that the joints form an ideal incubator for pathogenic germs and mildews.

The prior art also discloses using zinc material for protection from corrosion and destruction of outer surfaces of constructional elements located in seashore areas by algae or other similar sea organisms (U.S. Pat. No. 3,507,676 to McMahon).

Also is known using a "sacrificial" zinc coating having a first metal layer and an electro-conductive self-adhesive layer where the metal layer serves as anode and is destroyed prior than the corrosion can attain the protective element (U.S. Pat. No. 4,496,444 to Bagnulo).

Accordingly, it is an object of the present invention to provide a coating material for and a method of inhibiting pathogenic and saprophitic organisms on indoor surfaces of locations of medical, biological, and similar institutions.

In keeping with these objects and with others which will become apparent hereinafter, one feature of the present invention resides, briefly stated, in a coating material for inhibiting pathogenic and saprophitic organisms, which comprises a thin zinc lamina which possesses anti-bacterial, anti-virulent, anti-fungal and anti-mold properties.

When the coating material is designed in accordance with the present invention, the layer of zinc provides the effect that the existence and multiplication of bacteria, viruses, fungi and mildews is prevented or at least inhibited and in most cases they are destroyed by the presence of the zinc.

In accordance with another advantageous feature of the present invention, the coating material is formed as a foil, which includes the abovementioned thin layer of zinc and in addition has a self-adhesive and/or pressure-sensitive film of glue on one side of the layer. Because of the very small thickness of the zinc layer and the self-adhesive layer, the coating material can be easily applied to all kinds of objects and walls, in particular walls of medical and other similar facilities.

A further feature of the present invention is a method of inhibiting pathogenic and saprophitic organisms, which includes the steps of applying a coating material having a thin layer consisting of zinc, on respective indoor surfaces of locations of medical, biological and similar institutions.

The novel features of the invention are set forth in particular in the appended claims. The invention itself, however, will be best understood from the following description of preferred embodiments.

DESCRIPTION OF THE PREFERRED EMBODIMENTS

A coating material according to the invention for inhibiting pathogenic and saprophitic organisms includes a very thin zinc lamina which possesses anti-bacterial, anti-virulent, anti-fungi and anti-mold properties. The thickness of the zinc lamina is preferably between 0.08 and 0.1 mm. The zinc lamina can be in form of a foil or a tape.

The zinc lamina is provided with a self-sticking layer on one of its sides. The self-sticking layer is coextensive with the zinc layer or in other words is applied over the whole surface of the latter. The self-sticking layer can be formed as a self-adhesive film of glue. It can also be formed as a pressure-sensitive film of glue. This self-sticking adhesive film is preferably composed of an acrylic or elastomeric glue. The adhesive film can have a thickness preferably between 0.04 and 0.6 mm.

For preventing electrostatic charges on the surface of the zinc layer which constitutes a hazard in certain surrounding, for example, reanimation rooms, the self-sticking layer is composed of an electrically conductive adhesive. Such a layer can be formed by mixing of granules of suitable size. More particularly, the adhesive material is mixed with granules of an electrically conductive material in particular zinc granules to form the adhesive layer. The granules can also be composed of a different electrically conductive material. The additional electrically conductive materials in question can include, for example, copper, aluminum, graphite, etc. When the coating material in accordance with the present invention is applied to a respective surface, the zinc granules in the adhesive layer provide for an earthing-contact between the main layer of zinc and the wall.

The adhesive layer is protected on its side which faces away of the zinc lamina with a silicon release backing, a removable protective paper or a silicon film. Before applying the coating lamina, the covering layer is removed.

Since the whole coating material is formed as a foil or a tape of suitable sizes it can be fixed immediately on surfaces to be covered, such as walls, in an easy way, either manually or mechanically. The visible surface of the zinc layer which can be formed as rolled zinc, is smooth and thus free of incubating areas for bacteria, pathogenic germs and mildews. This smooth surface is suitable for complete and quick cleaning and disinfection, if it is necessary.

Tests have been conducted in which similar bacterial solutions were brought in contact with the zinc layer of the inventive coating material and other preventive elements. The tests have shown that when the zinc coating material in accordance with the present invention is used for a predetermined time, remarkably fewer colonies of bacteria are formed.

While the invention has been illustrated and described as embodied in a coating material for inhibiting pathogenic and saprophitic microorganisms, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of inhibiting accretion and multiplication of pathogenic and saprophitic organisms on inner walls of medical or biological institutions susceptible to pollutions caused by pathogenic and saprophitic organisms, said method comprising the steps of providing a thin zinc lamina having anti-bacterial, anti-virulent, anti-fungal, and anti-mold properties, and an adhesive layer applied to one of opposite surfaces of the zinc lamina; and applying the zinc lamina on the inner walls of medical or biological institutions on which pathogenic and saprophitic organisms are to be inhibited.

2. A method as defined in claim 1, wherein said adhesive layer is formed as an electro-conductive adhesive layer.

3. A method as defined in claim 1, wherein said zinc lamina is formed as a foil.

4. A method as defined in claim 1, wherein said zinc lamina is formed as a tape.

5. A method as defined in claim 1, wherein said adhesive layer is coextensive with said one zinc surface.

6. A method as defined in claim 1, wherein said adhesive layer is composed of a self-adhesive material.

7. A method as defined in claim 1, wherein said adhesive layer is composed of a pressure-sensitive adhesive material.

8. A method as defined in claim 1, wherein said zinc lamina is formed as a rolled zinc layer.

9. A method as defined in claim 1, wherein said zinc lamina has a thickness of between 0.08 and 0.1 mm.

10. A method as defined in claim 1, wherein said adhesive layer is composed of an acrylic glue.

11. A method as defined in claim 1, wherein said adhesive layer is composed of an elastomeric glue.

12. A method as defined in claim 1, wherein said adhesive layer has a thickness of substantially 0.04 and 0.6 mm.

13. A method as defined in claim 1, wherein said adhesive layer is composed of a material which includes an adhesive and a plurality of metal electrically conductive granules.

14. A method as defined in claim 13, wherein said metal granules of said adhesive layer are composed of zinc.

15. A method as defined in claim 1, wherein said adhesive layer has one surface which faces toward said one zinc surface and another surface which faces away of said one zinc lamina, a removable covering layer being applied to said another surface of said adhesive layer prior to application to the wall.

16. A method as defined in claim 15, wherein said covering layer is composed of silicon paper.

17. A method as defined in claim 15, wherein said covering layer is composed of a silicon film.

* * * * *